United States Patent
Adderly et al.

(10) Patent No.: US 9,583,401 B2
(45) Date of Patent: Feb. 28, 2017

(54) NANO DEPOSITION AND ABLATION FOR THE REPAIR AND FABRICATION OF INTEGRATED CIRCUITS

(71) Applicant: International Business Machines Corporation, Armonk, NY (US)

(72) Inventors: Shawn A. Adderly, Essex Junction, VT (US); Jeffrey P. Gambino, Westford, VT (US); Eric A. Joseph, White Plains, NY (US); Anthony C. Speranza, Gilbert, SC (US)

(73) Assignee: International Business Machines Corporation, Armonk, NY (US)

( * ) Notice: Subject to any disclaimer, the term of this patent is extended or adjusted under 35 U.S.C. 154(b) by 384 days.

(21) Appl. No.: 14/179,099

(22) Filed: Feb. 12, 2014

(65) Prior Publication Data

US 2015/0228548 A1    Aug. 13, 2015

(51) Int. Cl.

| | |
|---|---|
| G01L 21/30 | (2006.01) |
| G01R 31/00 | (2006.01) |
| H01L 21/66 | (2006.01) |
| H01L 21/768 | (2006.01) |
| H01J 37/32 | (2006.01) |
| H05H 1/24 | (2006.01) |
| C23C 16/04 | (2006.01) |
| C23C 16/513 | (2006.01) |
| G01N 23/225 | (2006.01) |

(52) U.S. Cl.
CPC ............. *H01L 22/12* (2013.01); *C23C 16/04* (2013.01); *C23C 16/513* (2013.01); *G01N 23/2252* (2013.01); *H01J 37/32082* (2013.01); *H01J 37/32366* (2013.01); *H01J 37/32449* (2013.01); *H01J 37/32568* (2013.01); *H01L 21/76892* (2013.01); *H01L 21/76894* (2013.01); *H05H 1/2406* (2013.01); *G01N 2223/6116* (2013.01); *G01N 2223/645* (2013.01); *H01J 2237/2817* (2013.01); *H05H 2001/2431* (2013.01)

(58) Field of Classification Search
USPC .......................................................... 216/59
See application file for complete search history.

(56) References Cited

U.S. PATENT DOCUMENTS

| 4,908,226 A | 3/1990 | Kubena et al. |
|---|---|---|
| 5,103,102 A | 4/1992 | Economou et al. |

(Continued)

FOREIGN PATENT DOCUMENTS

DE    EP 1 868 255 A1    12/2007

OTHER PUBLICATIONS

Baird et al., "Ultraviolet laser repair of advanced semiconductor memory devices", Technical Digest and Summaries of papers presented at the IEEE Conference on Lasers and Electro-Optics (CLE0'01), May 8, 2001, p. 230.

(Continued)

*Primary Examiner* — Roberts Culbert
(74) *Attorney, Agent, or Firm* — Schmeiser, Olsen & Watts; Steven Meyers

(57) ABSTRACT

An apparatus for and methods of repairing and manufacturing integrated circuits using the apparatus. The apparatus, comprising: a vacuum chamber containing: a movable stage configured to hold a substrate; an inspection and analysis probe; a heat source; a gas injector; and a gas manifold connecting multiple gas sources to the gas injector.

10 Claims, 5 Drawing Sheets

(56) References Cited

U.S. PATENT DOCUMENTS

| | | |
|---|---|---|
| 5,173,441 A | 12/1992 | Yu et al. |
| 5,236,747 A | 8/1993 | Dessaux et al. |
| 5,414,519 A | 5/1995 | Han |
| 5,483,490 A | 1/1996 | Iwai et al. |
| 6,427,324 B1 | 8/2002 | Franklin et al. |
| 6,753,253 B1 | 6/2004 | Takahashi et al. |
| 7,521,367 B2 | 4/2009 | Crawford |
| 7,666,690 B2 | 2/2010 | Lee et al. |
| 7,795,154 B2 | 9/2010 | Tanaka et al. |
| 2010/0062182 A1 | 3/2010 | Arai et al. |
| 2012/0021132 A1 | 1/2012 | Shimizu et al. |
| 2015/0128098 A1* | 5/2015 | Chang ................ G06F 17/5081 716/52 |

OTHER PUBLICATIONS

Chen et al., "An Automated System for Thin Film Circuit Repair", IPCOM000103241D, Original Publication Date Aug. 1, 1990; IP.com Electronic Publication Date Mar. 17, 2005; 2 pages.

Lin et al., "Focused Electron and Ion Beam Repair Strategies for Wafer-Scale Interconnections in Thin Film Packaging", Thin Solid Films, 166; pp. 121-130 (1988); Paper presented at the 15th International Conference on Metallurgical Coatings, San Diego, CA, Apr. 11-15, 1988.

Iza et al., "Microplasmas: Sources, Particle Kinetics, and Biomedical Applications", Plasma Process. Polym., vol. 5, Apr. 8, 2008, pp. 322-344.

\* cited by examiner

NANO DEPOSITION AND ABLATION FOR THE REPAIR AND FABRICATION OF INTEGRATED CIRCUITS

BACKGROUND

The present invention relates to the field of integrated circuit manufacture; more specifically, it relates to an apparatus and a method for manufacture and repair of microelectronic circuits.

Modern integrated circuits utilize microscopic wiring to interconnect semiconductor devices such as transistors into circuits. Often defects in the wires occur that render the integrated circuit non-functional or unreliable. Additionally, it is very expensive to customize integrated circuits because of the cost of masks. Accordingly, there exists a need in the art to mitigate the deficiencies and limitations described hereinabove.

BRIEF SUMMARY

A first aspect of the present invention is an apparatus, comprising: a vacuum chamber containing: a movable stage configured to hold a substrate; an inspection and analysis probe; a heat source; a gas injector; and a gas manifold connecting multiple gas sources to the gas injector.

A second aspect of the present invention is a method, comprising: (a) providing an apparatus including: a vacuum chamber containing a movable stage configured to hold a substrate, an inspection and analysis probe, a heat source; a gas injector and a gas manifold, the gas manifold connecting multiple gas sources to the gas injector; (b) loading a substrate onto the movable stage; (c) scanning the substrate for defects using the inspection and analysis probe; (d) if a defect is found determining if it is (i) a short or extension between wires, (ii) an open or notch in a wire, or (iii) a void in a dielectric layer between the wires; determining a chemical composition of the defect; selecting a gas from the multiple gas sources for repairing the defect; if the defect is a short or extension between wires either laser abating or plasma etching the defect using the selected gas; if the defect is an open or notch in a wire, depositing a conductive material to repair the defect using the selected gas; and if the defect is a void in a dielectric layer between wires, depositing a dielectric material to repair the defect using the selected gas; and (e) repeating steps (c) and (d) until no defects are found.

A third aspect of the present invention is a method, comprising: (a) providing an apparatus including: a controller and a vacuum chamber, the vacuum chamber containing a movable stage configured to hold a substrate, an inspection and analysis probe, a heat source; a gas injector and a gas manifold, the gas manifold connecting multiple gas sources to the gas injector; (b) loading a substrate onto the movable stage; (c) loading a wiring scheme into the controller; (d) selecting a wiring instruction from the wiring scheme and determining if the instruction is to connect wires or cut wires and selecting a gas from the multiple gas sources; (e) if the instruction is to cut a wire, either laser abating or plasma etching the wire using the selected gas or if the instruction is to connect wires, depositing a conductive material between the wires to connect the wires; and (f) repeating steps (c) and (e) until no there are no further instructions.

These and other aspects of the invention are described below.

BRIEF DESCRIPTION OF THE DRAWINGS

The features of the invention are set forth in the appended claims. The invention itself, however, will be best understood by reference to the following detailed description of illustrative embodiments when read in conjunction with the accompanying drawings, wherein:

DETAILED DESCRIPTION

The embodiments of the present invention repair defects and form custom wiring having wire widths in the several hundreds of nanometers range using nano plasma deposition and nano ablation.

Figure 1:
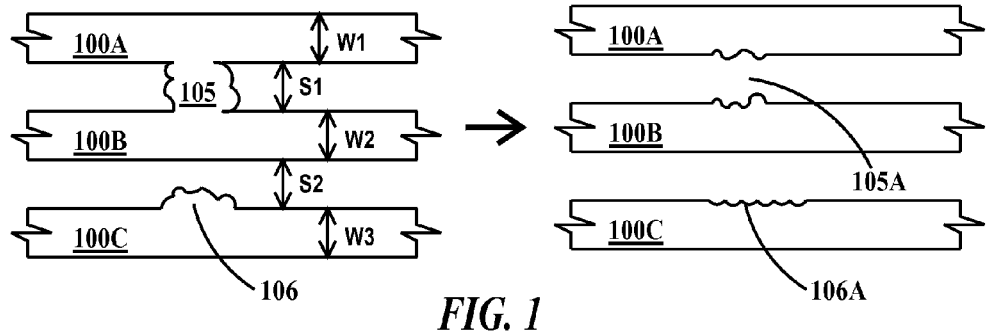
FIG. 1 is a top view illustrating the ablation of a short between two wires according to embodiments of the present invention.

FIG. 1 is a top view illustrating the ablation of a short between two wires according to embodiments of the present invention. On the left side of FIG. 1, three electrically wires 100A, 100B and 100C are illustrated. A short defect 105 electrically connects wires 100A and 100B and an extension defect 106 protrudes from wire 100C toward 100B. Wire 100A has a width W1, wire 110B has a width W2, and wire 100C has a width W3. Wire 100A is spaced a distance S1 from wire 100B and wire 100B is spaced a distance S2 from wire 100C. In one example, at least one of W1, W2, W3, S1 and S2 are less than one micron. In one example, at least one of W1, W2, W3, S1 and S2 are less than 500 nanometers. Wires 100A, 100B and 100C may comprise copper, aluminum, tungsten, titanium, tungsten nitride, titanium nitride or combinations thereof. On the right side of FIG. 1, an ablation process has been performed to remove short defect 105 and extension defect 106 leaving behind respective repairs 105A and 106A.

Figure 2:
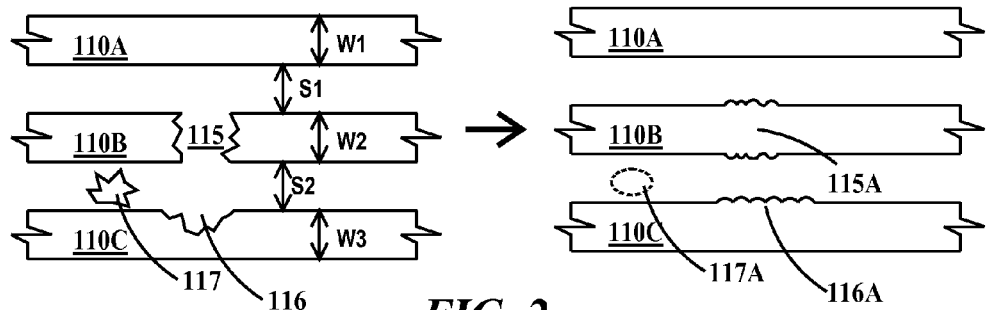
FIG. 2 is a top view illustrating deposition to repair an open in a wire according to embodiments of the present invention.

FIG. 2 is a top view illustrating deposition to repair an open in a wire according to embodiments of the present invention. On the left side of FIG. 2, three electrically wires 110A, 110B and 110C are illustrated. An open defect 115 electrically breaks wire 110B, a notch defect 116 exists in wire 110C and a void defect 117 exists in the dielectric between wires 110C and 110B. Wire 110A has a width W1, wire 110B has a width W2, and wire 110C has a width W3. Wire 110A is spaced a distance S1 from wire 110B and wire 110B is spaced a distance S2 from wire 110C. In one example, at least one of W1, W2, W3, S1 and S2 are less than one micron. In one example, at least one of W1, W2, W3, S1 and S2 are less than 500 nanometers. Wires 110A, 110B and 110C may comprise copper, aluminum, tungsten, titanium, tungsten nitride, titanium nitride or combinations thereof. On the right side of FIG. 2, two deposition processes have been performed to form an electrically conductive repair 115A on wire 110B, an electrically conductive repair 116A on wire 110C and a dielectric repair 117A between wires 110C and 110B. In one example, repairs 115A and 116A comprise aluminum, copper or tungsten. In one example, repair 117A comprise a silicon oxide or silicon nitride.

Figure 3:
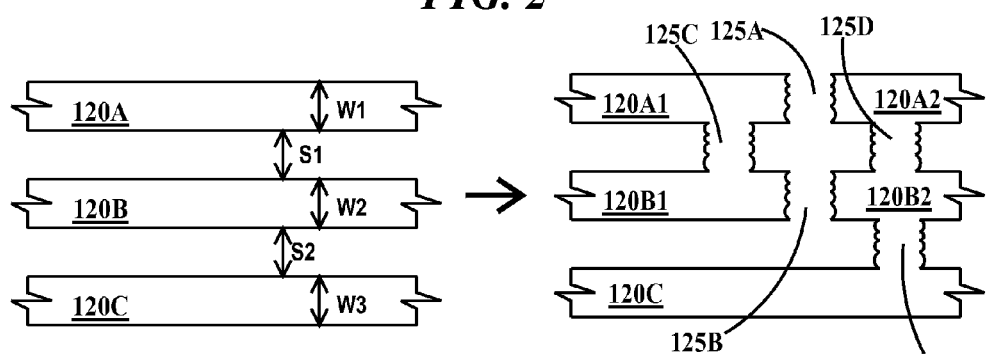
FIG. 3 is a top view illustrating fabrication of custom wiring according to embodiments of the present invention.

FIG. 3 is a top view illustrating fabrication of custom wiring according to embodiments of the present invention. On the left side of FIG. 3, three electrically wires 120A, 120B and 120C are illustrated. Wire 120A has a width W1, wire 110B has a width W2, and wire 120C has a width W3. Wire 120A is spaced a distance S1 from wire 120B and wire 120B is spaced a distance S2 from wire 120C. In one example, at least one of W1, W2, W3, S1 and S2 are less than one micron. In one example, at least one of W1, W2, W3, S1 and S2 are less than 500 nanometers. On the right side of FIG. 2, an ablation process has been performed to break wire 120A into wires 120A1 and 120A2 and to break wire 120B into wires 120B1 and 120B2 by forming openings 125A and 125B respectively. Also, a deposition process has been performed to form an electrically conductive connection 125C between wires 120A1 and 120B1, an electrically conductive connection 125D between wires 120A2 and 120B2, and an electrically conductive connection 125E between wires 120B2 and 120C. In one example, connections 125C, 125D and 125E comprise aluminum, copper or tungsten. In effect, a custom wiring pattern has been formed from wires 120A, 120B and 120C.

Figure 4:
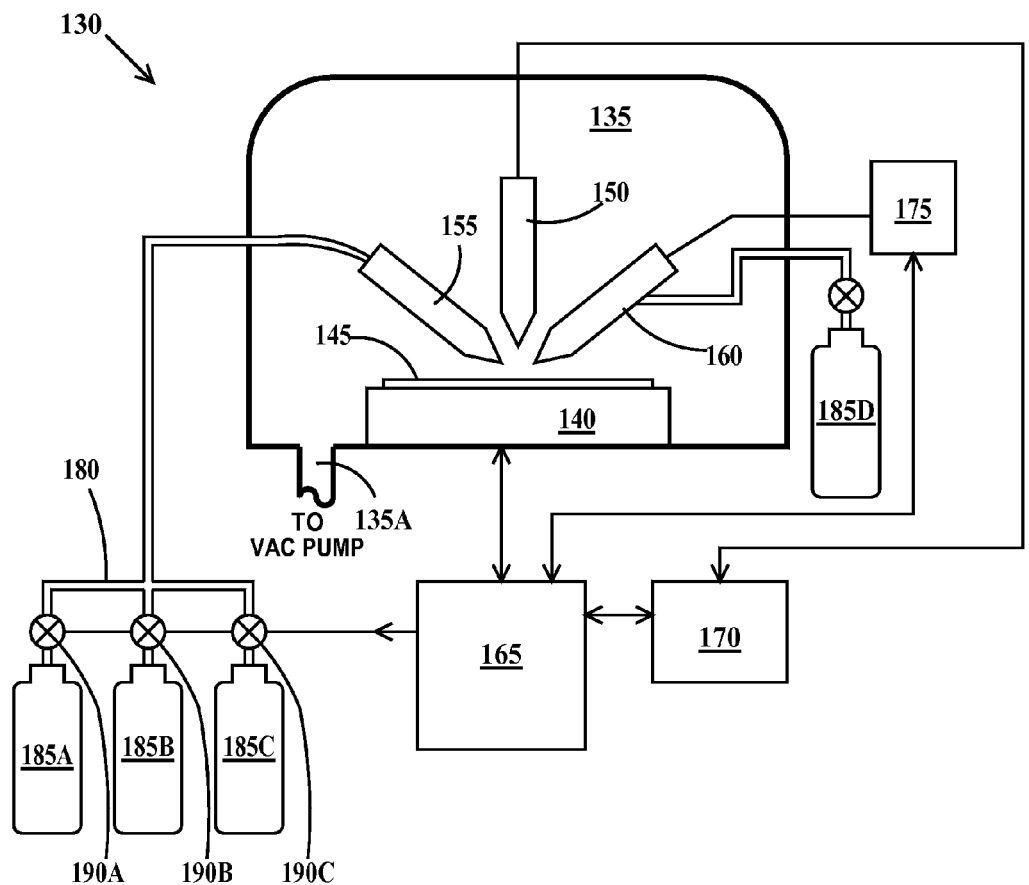
FIG. 4 is a schematic diagram of a first fabrication and repair apparatus according to embodiments of the present invention.

FIG. 4 is a schematic diagram of a first fabrication and repair apparatus according to embodiments of the present invention. In FIG. 4, an apparatus 130 includes a vacuum chamber 135 having a vacuum port 135A, and XYZ stage 140 within the vacuum chamber for holding substrate 145, an inspection and analysis probe 150, a gas injector 155 and a heat source 160. In one example, heat source 160 is a micro-probe or a micro-plasma probe. In the case of a micro-plasma probe, a non-reactive gas source 185D is supplied. In one example, substrate 145 is a semiconductor substrate (e.g., wafer) commonly used for the fabrication of integrated circuits. Apparatus 130 also includes a main controller 165, an inspection and analysis controller 170, a power supply 175, a gas manifold 180 connected to gas source 185A, 185B and 185C by respective solenoid valves 190A, 190B and 190C. Manifold 180 is connected to gas injector 155. Controller 165 is also connected to XYZ stage 140 and controls movement of the XYZ stage. The position of gas injector 155 and heat source 160 are adjusted (maybe fixed or movable) to converge the gas stream and laser spot or plasma to the same point on substrate 145.

Inspection and analysis probe 150 is connected to inspection and analysis controller 170 and comprises a real time inspection and analysis system configured to scan substrate 145, recognize defects, and to chemically analyze the composition of any defect found. Inspection and analysis probe 150 comprises a scanning electron microscope (SEM) probe connected to an image recognition system within inspection and analysis controller 170 and an energy-dispersive X-ray (EDX) spectrophotometer probe connected to an EDX module within inspection and analysis controller 170. By comparing a stored design pattern to the scanned pattern, opens and shorts and other defects (such as notches in wiring that reduce the cross-sectional area of the wire and wire extensions that reduce the space between adjacent wires) can be detected. Additionally, voids in the dielectric layer between wires may be detected. The defect can then be analyzed for chemical composition. Thus the type of defect, its location and its composition (or the composition surrounding the defect) is determined.

Power supply 175 is connected between heat source 160 and controller 165. Solenoid valves 190A, 190B and 190C are also connected to controller 165. When a defect is found by the inspection and analysis system, its type is determined (e.g., open, short, notch, extension, hole), its position is determined, and its composition is determined. For a short or extension, the composition of the defect is determined, for an open or notch, the composition of the wire is determined. Controller 165 then determines the power setting for power supply 175 and which gas to be supplied to gas injector 155 to affect a repair. For example, when heat source 160 is a micro-laser and the defect is a short or extension, the wattage of the laser (based on the size and composition of the defect) is set to ablate the defect. When the heat source is a micro-plasma probe, the radio frequency (RF) voltage, direct current (DC) bias, and inert gas and flow rate are set to sputter etch the defect. An etchant gas may also be supplied to gas injector 155 in which case the defect is plasma or reactive ion etched. When the heat source is a micro-laser and the defect is an open or notch or hole, not only is the wattage of the micro-laser set but also a deposition gas and flow rate is set (based on the size of the open or notch and composition of the wire containing the defect).

Examples of inert gases include nitrogen, argon and neon. Examples of etchant gases include chloro and fluoro hydrocarbons, oxygen, and hydrogen. Examples of metal deposition gases include aluminum alkyls such as triisobutylaluminum (TIBA) and tri methyl aluminum (TMA), aluminum alkyl hydrides such as dimethylaluminum hydride (DMAH), copper beta-diketonates, copper (II) dialykldithiocarbamate complexes, and tungsten hexafluoride. Additionally, defects in the dielectric between wires may be repaired by deposition of a dielectric material from tetraethylorthosilicate, silane and nitrogen tetra fluoride.

Figure 5:
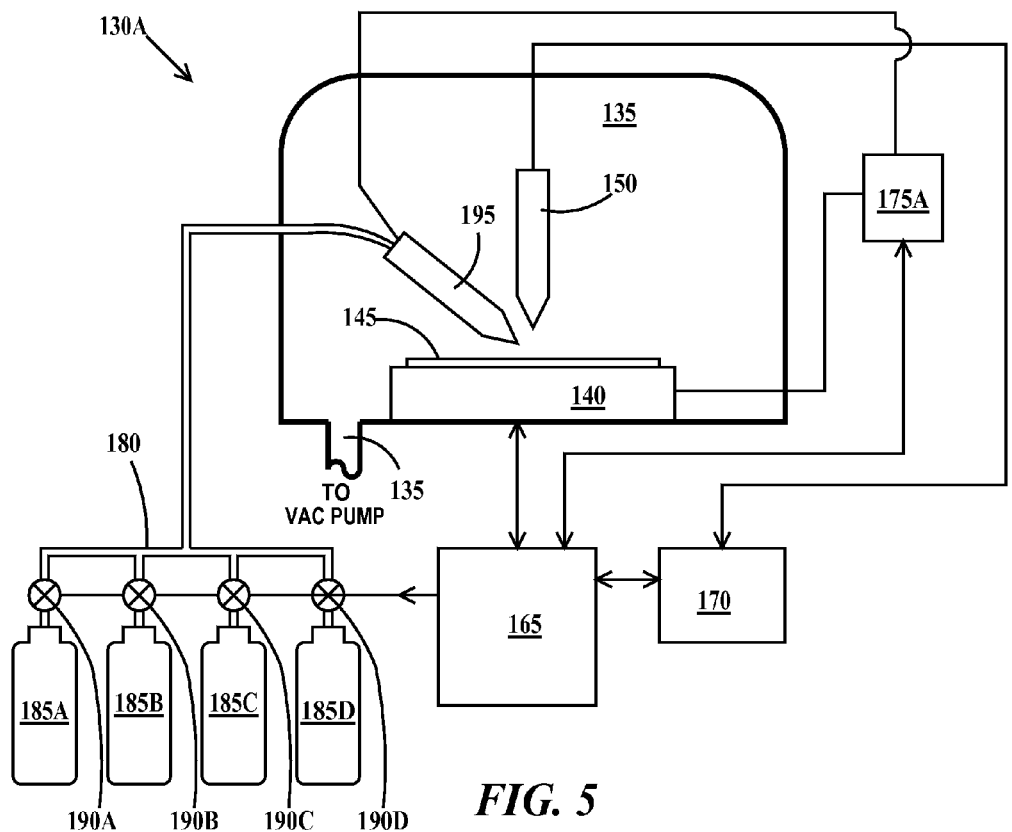
FIG. 5 is a schematic diagram of a second fabrication and repair apparatus according to embodiments of the present invention.

FIG. 5 is a schematic diagram of a second fabrication and repair apparatus according to embodiments of the present invention. FIG. 5 is similar to FIG. 4, except apparatus 130A utilizes the separate gas injector 155 and a heat source 160 of FIG. 4 are replaced with a single micro-plasma nozzle 195 and inert gas source 185D is connected to manifold 180 by solenoid valve 190D. Also, power supply 170 of FIG. 4 is replaced by power supply 175A which is connected to micro-plasma nozzle 195. Thus ablation and deposition are performed using only micro-plasma nozzle 195.

Figure 6:
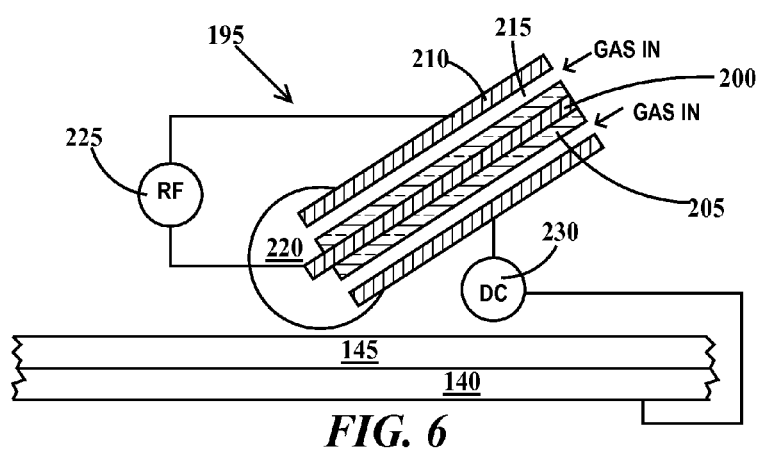
FIG. 6 is a schematic cross-section of a nano plasma nozzle of FIG. 5.

FIG. 6 is a schematic cross-section of a nano plasma nozzle 195 of FIG. 5. In FIG. 6, micro-plasma nozzle 195 includes a central axial electrode 200, a coaxial insulator 205 and a coaxial outer electrode 210. A coaxial gap 215 between coaxial insulator 205 and coaxial outer electrode 210 also a selected gas or gas mixture from manifold 180 of FIG. 5 to pass through micro-plasma nozzle 195 to form a plasma 220 above substrate 145. An RF source from power supply 175 (see FIG. 5) is connected between central axial electrode 200 and coaxial outer electrode 210. A DC power source 230 from power supply 175 (see FIG. 5) is connected between XYZ stage 140 and coaxial outer electrode 210. Thus micro-plasma nozzle 195 can perform plasma etching or reactive ion etching or plasma enhanced deposition.

Figure 7:
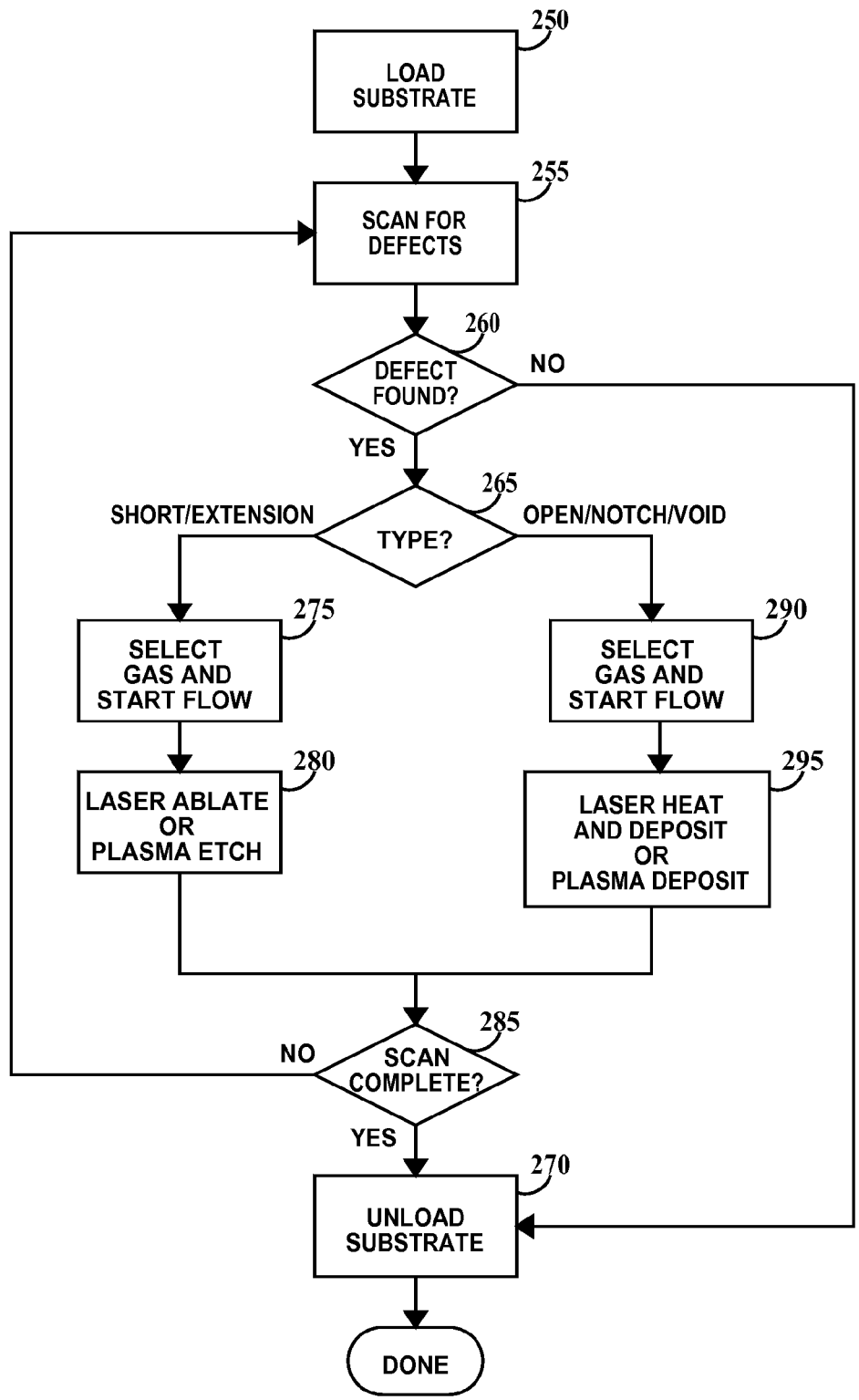
FIG. 7 is a flowchart of a method of repairing an integrated circuit according to embodiments of the present invention.

FIG. 7 is a flowchart of a method of repairing an integrated circuit according to embodiments of the present invention. In step 250, a semiconductor substrate is loaded onto the stage of the apparatus illustrated in FIG. 4 or 5 and described supra. In step 255, the defect inspection scan is started. The wiring structure on the substrate is inspected and any defect found identified using an image recognition system. In step 260, if a defect is found, the method proceeds to step 265, otherwise the method proceeds to step 270. In step 265, the type of defect is identified, either a short/extension defect or open/notch/void defect. If the defect is a short/extension defect the method proceeds to step 275. In step 275, the gas and gas flow that will be used to repair the defect by laser ablation or plasma etching is selected as are the power settings for the laser/plasma heat source or micro-plasma nozzle. In step 280, the defect is repaired by laser ablation or plasma etching. Next, in step 285, it is determined if the defect scan is complete. If the scan is complete, the method proceeds to step 270 where the substrate is unloaded, otherwise the method loops back to step 255 and the scan is continued. Returning to step 265, if the defect is open/notch/void the method proceeds to step 290. In step 290, the gas and gas flow that will be used to repair the defect by deposition is selected as are the power settings for the laser/plasma heat source or micro-plasma nozzle. In step 295, the defect is repaired by deposition of material to bridge the open or fill the notch or void. The method then proceeds to step 285 described previously.

Figure 8:
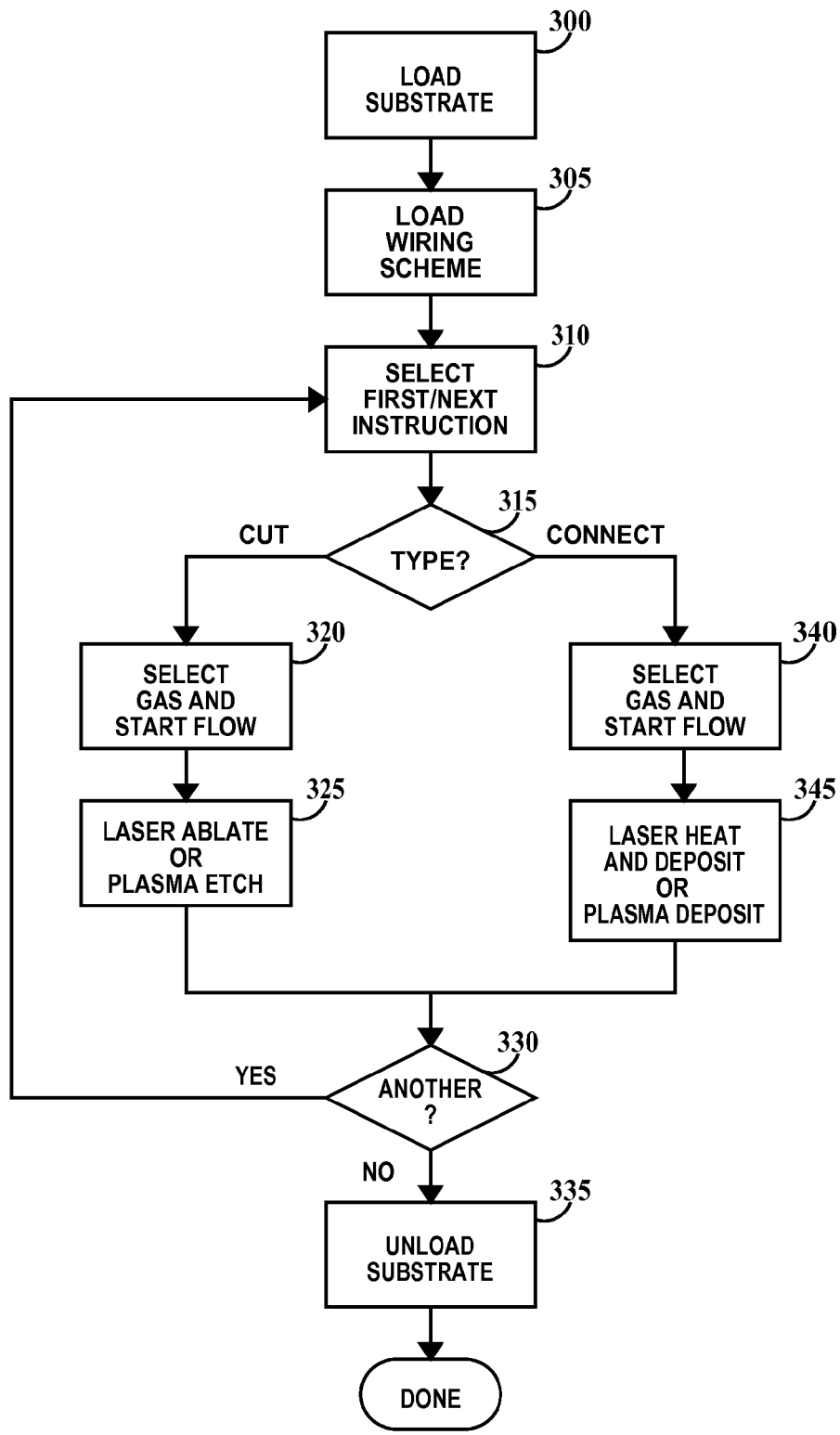
FIG. 8 is a flowchart of a method of custom wiring of an integrated circuit according to embodiments of the present invention.

FIG. 8 is a flowchart of a method of custom wiring of an integrated circuit according to embodiments of the present invention. In step 300, a semiconductor substrate is loaded onto the stage of the apparatus illustrated in FIG. 4 or 5 and described supra. In step 305, the wiring scheme is loaded. Next, in step 310, the first/next instruction is selected, the stage is moved to the location indicated by the instruction, and the method proceeds to step 315. In step 315, the type of instruction is identified, either a wiring connection or a wiring cut. If the instruction is to cut a wire then the method proceeds to step 320. In step 320, the gas and gas flow that will be used to cut the wire by laser ablation or plasma etching is selected as are the power settings for the laser/plasma heat source or micro-plasma nozzle. In step 325, the wire is cut by laser ablation or plasma etching. Next, in step 330, it is determined if there is another instruction. If there is another instruction, the method proceeds to step 310, otherwise the method proceeds to step 335 where the substrate is unloaded. Returning to step 315, if the instruction is to connect wires then the method proceeds to step 340. In step 340, the gas and gas flow that will be used to connect the wires by deposition is selected as are the power settings for the laser/plasma heat source or micro-plasma nozzle. In step 345, the wires are connected by deposition of conductive material. The method then proceeds to step 330 described previously.

When either the apparatus of FIG. 4 or the apparatus of FIG. 5 are used to generate wiring schemes, the inclusion of EDX capability in the apparatus is optional.

Thus, the embodiments of the present invention provide an apparatus and method for repairing defects and forming custom wiring having wire widths in the several hundreds of nanometers range using nano plasma deposition and nano ablation.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
    (a) providing an apparatus including:
        a vacuum chamber containing a movable stage configured to hold a substrate, an inspection and analysis probe, a heat source, a gas injector and a gas manifold, said gas manifold connecting multiple gas sources to said gas injector;
    (b) loading a substrate onto said movable stage;
    (c) scanning said substrate for defects using said inspection and analysis probe;
    (d) if a defect is found determining if it is (i) a short or extension between wires, (ii) an open or notch in a wire, or (iii) a void in a dielectric layer between said wires;
        determining a chemical composition of said defect;
        selecting a gas from said multiple gas sources for repairing said defect;
        if said defect is a short or extension between wires either laser abating or plasma etching said defect using said selected gas;
        if said defect is an open or notch in a wire, depositing a conductive material to repair said defect using said selected gas; and
        if said defect is a void in a dielectric layer between wires, depositing a dielectric material to repair said defect using said selected gas; and
    (e) repeating steps (c) and (d) until no defects are found.

2. The method of claim 1, wherein said inspection and analysis probe includes a scanning electron microscope probe connected to an image recognition system and (c) includes using said image recognition system to determine if a defect exists.

3. The method of claim 1, wherein said inspection and analysis probe includes an energy dispersive X-ray spectrophotometer probe and said determining a chemical composition of said defect includes using said dispersive X-ray spectrophotometer probe to determine said chemical composition of said defect.

4. The method of claim 1, wherein said substrate is a semiconductor substrate.

5. The method of claim 1, wherein said multiple gas sources comprise:
    at least one inert gas comprising one or more of nitrogen, argon and neon; and
    at least one etchant gas comprising one or more of chloro and fluoro hydrocarbons, oxygen and hydrogen; and
    at least one metal deposition gas comprising one or more of aluminum alkyls, triisobutylaluminum, tri methyl aluminum, aluminum alkyl hydrides, dimethylaluminum hydride, copper beta-diketonates, copper (II) dialykldithiocarbamate complexes, and tungsten hexafluoride.

6. The method of claim 5, wherein said multiple gas sources further comprise:
    at least one dielectric deposition gas comprising one or more of tetraethylorthosilicate, silane and nitrogen tetra fluoride.

7. A method, comprising:
    (a) providing an apparatus including:
        a controller and a vacuum chamber, said vacuum chamber containing a movable stage configured to hold a substrate, an inspection and analysis probe, a heat source; a gas injector and a gas manifold, said gas manifold connecting multiple gas sources to said gas injector;

(b) loading a substrate onto said movable stage;

(c) loading a wiring scheme into said controller;

(d) selecting a wiring instruction from said wiring scheme and determining if the instruction is to connect wires or cut wires and selecting a gas from said multiple gas sources;

(e) if said instruction is to cut a wire, either laser abating or plasma etching said wire using said selected gas or if said instruction is to connect wires, depositing a conductive material between said wires to connect said wires; and (f) repeating steps (c) and (e) until no there are no further instructions.

8. The method of claim 7, wherein said inspection and analysis probe includes a scanning electron microscope probe connected to an image recognition system.

9. The method of claim 7, wherein said inspection and analysis probe includes an energy dispersive X-ray spectrophotometer probe and said determining a chemical composition of said defect includes using said dispersive X-ray spectrophotometer probe to determine said chemical composition of said defect.

10. The method of claim 7, wherein said substrate is a semiconductor substrate and wherein said multiple gas sources comprise:

at least one inert gas comprising one or more of nitrogen, argon and neon; and at least one etchant gas comprising one or more of chloro and fluoro hydrocarbons, oxygen and hydrogen; and at least one metal deposition gas comprising one or more of aluminum alkyls, triisobutylaluminum, tri methyl aluminum, aluminum alkyl hydrides, dimethylaluminum hydride, copper beta-diketonates, copper (II) dialykldithiocarbamate complexes, and tungsten hexafluoride.

* * * * *